(12) United States Patent
Fukui et al.

(10) Patent No.: US 9,416,276 B2
(45) Date of Patent: Aug. 16, 2016

(54) METHOD FOR PRODUCING CONTRAST AGENT

(71) Applicant: CANON KABUSHIKI KAISHA, Tokyo (JP)

(72) Inventors: Tatsuki Fukui, Yokohama (JP); Atsushi Takahashi, Kyoto (JP); Daisuke Sasaguri, Yokohama (JP); Fumiko Tomatsu, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/534,111

(22) Filed: Nov. 5, 2014

(65) Prior Publication Data

US 2015/0126749 A1     May 7, 2015

(30) Foreign Application Priority Data

Nov. 7, 2013 (JP) ................. 2013-231576

(51) Int. Cl.
*C09B 23/08* (2006.01)

(52) U.S. Cl.
CPC ................... *C09B 23/086* (2013.01)

(58) Field of Classification Search
None
See application file for complete search history.

(56) References Cited

U.S. PATENT DOCUMENTS

2015/0157741 A1*   6/2015   Yamauchi et al.

FOREIGN PATENT DOCUMENTS

| JP | 9-124599 A | 5/1997 |
| JP | 2012-520856 A | 9/2012 |

OTHER PUBLICATIONS

R.Weigand etal., "Degree of aggregation of indocyanine green in aqueous solutions determined by Mie scattering", Chemical Physics vol. 220,Issue 3,p. 373-384(1997).

* cited by examiner

*Primary Examiner* — Michael Barker
*Assistant Examiner* — Po-Chih Chen
(74) *Attorney, Agent, or Firm* — Canon U.S.A., Inc. IP Division (57) ABSTRACT

A method for producing a contrast agent includes the reaction step of allowing a cyanine dye containing a naphthyl group and a carboxyl or carboxylate group to react with a polyethylene glycol containing an amino group in an organic solvent to form a conjugate, and the purification step of purifying the conjugate using an organic solvent.

10 Claims, 3 Drawing Sheets

METHOD FOR PRODUCING CONTRAST AGENT

BACKGROUND OF THE INVENTION

1. Field of the Invention

The present invention relates to a method for producing a contrast agent.

2. Description of the Related Art

Fluorescent imaging and photoacoustic imaging have received attention as optical imaging methods capable of noninvasive diagnosis in recent years.

Fluorescent imaging is a method of detecting fluorescence emitted from a fluorescent dye by irradiating the fluorescent dye with light and is broadly used. Photoacoustic imaging is a method of imaging an object by irradiating the object with light, and detecting the intensity of acoustic waves generated by volume expansion resulting from the emission of heat from the molecules of the irradiated object and the position where the acoustic waves have been generated. In the fluorescent imaging and photoacoustic imaging, a dye may be used as a contrast agent for increasing the intensity of fluorescence or acoustic waves from a targeted site.

PCT Japanese Translation Patent Publication No. 2012-520856 discloses a contrast agent used for photoacoustic imaging and optical imaging and containing a conjugate of a cyanine dye and a polyethylene glycol (hereinafter may be abbreviated as PEG). In order to form the conjugate, Cy7-NHS (N-hydroxysuccinimide) ester (formula (1)), which is a cyanine dye difficult to form aggregates in water, is combined with a PEG containing amino groups at both ends in water. Then, the reaction product is purified by reversed phase chromatography using an aqueous solution.

(1)

If a cyanine dye containing a hydrophobic portion such as a naphthyl group is combined with a PEG containing an amino group, the cyanine dye is required to have a functional group capable of reacting with the amino group, such as carboxy or N-hydroxysuccinimide ester.

While N-hydroxysuccinimide esters can react with the amino group without using a condensing agent, the reactivity of the N-hydroxysuccinimide esters decreases with time. From the viewpoint of maintaining the reactivity of the cyanine dye with the amino group, therefore, a cyanine dye containing a carboxyl group is advantageously used.

Unfortunately, conjugates of a cyanine dye containing a carboxyl group and partially having a hydrophobic structure such as the naphthyl group and a PEG containing an amino group are difficult to purify by reversed phase chromatography using water or the like because the particles of the dye aggregate together in the column.

In order to increase the dispersibility of the dye in water, a sulfo or sulfonate group may be introduced to change the structure of the dye. However, this can vary reactivity between the carboxyl group and the amino group and light emitting characteristics. Accordingly, it is desired to synthesize a conjugate using a cyanine dye tending to form aggregates in water without changing the structure of the cyanine dye so as to increase the dispersibility, and purify the conjugate.

SUMMARY OF THE INVENTION

Accordingly, aspects of the present invention provide a method for producing a contrast agent in which a conjugate of a cyanine dye tending to aggregate in water and a PEG containing an amino group can be easily purified.

According to an aspect of the present invention, a method is provided for producing a contrast agent containing a conjugate of a compound expressed by the following general formula (I) and a compound expressed by the following general formula (II). The method includes the step of allowing the compound expressed by general formula (I) with the compound expressed by general formula (II) to form the conjugate, and the step of purifying the conjugate using an organic solvent.

(I)

In general formula (I), $R_{101}$ to $R_{112}$ each represent a species selected form the group consisting of hydrogen and linear and branched alkyl groups having a carbon number in the range of 1 to 18. $L_{11}$ to $L_{17}$ each represent a group selected from the group consisting of CH and $CR_{15}$. $R_{15}$ represents a linear or branched alkyl group having a carbon number in the range of 1 to 18. $L_{11}$ to $L_{17}$ may form one of 4-membered to 6-membered rings. $R_{11}$ to $R_{14}$ each represent a species selected form the group consisting of hydrogen and linear and branched alkyl groups having a carbon number in the range of 1 to 18. $A_{11}$ and $B_{11}$ each represent a linear or branched alkylene group having a carbon number in the range of 1 to 18. $R_a$ represents an atom selected from the group consisting of hydrogen, sodium and potassium.

(II)

In general formula (II), $D_{11}$ represents a linear or branched alkylene group having a carbon number in the range of 1 to 18. $E_{11}$ represents a species selected from the group consisting of hydrogen, linear and branched alkoxy groups having a carbon number in the range of 1 to 18, and linear and branched alkyl groups having a carbon number in the range of 1 to 18. Also, m represents an integer in the range of 1 to 20, and n represents an integer in the range of 1 to 2,500.

According to another aspect of the present invention, a method is provided for producing a contrast agent. The method include the reaction step of allowing a cyanine dye containing a naphthyl group and at least one of carboxyl and carboxylate groups to react with a polyethylene glycol containing an amino group in an organic solvent to form a conjugate, and the purification step of purifying the conjugate using an organic solvent.

Further features of the present invention will become apparent from the following description of exemplary embodiments with reference to the attached drawings.

DESCRIPTION OF THE EMBODIMENTS

An exemplary embodiment of the present invention will now be described, but the invention is not limited to the disclosed embodiment.

A method for producing a contrast agent according to an embodiment of the present invention includes the following process steps:

(a) Reaction Step of allowing a cyanine dye expressed by general formula (I), which contains naphthyl groups and a carboxyl or carboxylate group, to react with a polyethylene glycol expressed by general formula (II), which contains an amino group, in an organic solvent to form a conjugate; and (b) Purification Step of purifying a solution containing the conjugate produced in the step of (a) using an organic solvent.

(I)

In general formula (I), $R_{101}$ to $R_{112}$ each represent a species selected form the group consisting of hydrogen and linear and branched alkyl groups having a carbon number in the range of 1 to 18. $L_{11}$ to $L_{17}$ each represent CH or $CR_{15}$. $R_{15}$ represents a linear or branched alkyl group having a carbon number in the range of 1 to 18. $L_{11}$ to $L_{17}$ may form one of 4-membered to 6-membered rings. $R_{11}$ to $R_{14}$ each represent a species selected form the group consisting of hydrogen and linear and branched alkyl groups having a carbon number in the range of 1 to 18. $A_{11}$ and $B_{11}$ each represent a linear or branched alkylene group having a carbon number in the range of 1 to 18. $R_a$ represents hydrogen, sodium or potassium.

(II)

In general formula (II), $D_{11}$ represents a linear or branched alkylene group having a carbon number in the range of 1 to 18. $E_{11}$ represents a species selected from the group consisting of hydrogen, linear and branched alkoxy groups having a carbon number in the range of 1 to 18, and linear and branched alkyl groups having a carbon number in the range of 1 to 18. Also, m represents an integer in the range of 1 to 20, and n represents an integer in the range of 1 to 2,500.

It is known that cyanine dyes containing a naphthyl group as shown in general formula (I) are easy to aggregate. For example, Chemical Physics Volume 220, Issue 3, pp. 373-384 (1997) describes the aggregation characteristics of indocyanine green, which is a cyanine dye containing naphthyl groups, in water.

The present inventors found that even if a cyanine dye containing a naphthyl group has a carboxyl group, which is a hydrophilic functional group, the cyanine dye easily forms aggregate in water, and that conjugates of the dye and a PEG are not easily purified with water or an aqueous solution. Accordingly, the present inventors thought that a process is effective in which a conjugate is formed by allowing a cyanine dye expressed by general formula (I) containing naphthyl groups and a carboxyl or carboxylate group to react with a PEG containing an amino group in an organic solvent, and then the conjugate is purified using an organic solvent.

The use of an organic solvent makes it difficult for the product to form aggregates during purification and facilitates the purification of the targeted conjugate of the cyanine dye and the PEG.

The entirety or part of the reaction step and the purification step may be simultaneously performed. More specifically, purification may be performed while the conjugate is being formed, or in a stage where the reaction for forming the conjugate has proceeded to some extent but is proceeding.

The method may further include the drying step of removing the solvent from the solution containing the purified conjugate after the purification step.

The method may further include the dispersion step of dispersing the product obtained through the drying step in a dispersion medium. Furthermore, the method may include the step of adding a pharmacologically acceptable additive, such as a vasodilator.

Reaction Step

The reaction step in the method of the present embodiment is not particularly limited as long as the reaction produces a conjugate of a cyanine dye expressed by general formula (I) containing a naphthyl group and a carboxyl or carboxylate group and a compound expressed by general formula (II) containing a polyethylene glycol.

In the reaction for forming the conjugate, the carboxyl or carboxylate group reacts with the amino group. This reaction may be performed by, for example, use of a condensing agent, condensation by forming a salt to dehydrate, use of a dehydrating agent, or a reaction of an acid chloride converted from the carboxyl group with the amino group.

Condensing agents that can be used include carbodiimide condensing agents and phosphoric acid-based condensing agents.

Examples of the carbodiimide condensing agents include N,N'-dicyclohexylcarbodiimide (DCC) and water-soluble carbodiimide (WSC).

The proportion of the condensing agent to be added is 0.1 or more, preferably 1 or more, on a mole basis relative to the compound expressed by general formula (I). The condensing agent may be used as the reaction solvent.

The proportion of the compound of general formula (I) used in the reaction step is preferably 0.1 to 50.0 on a mole basis relative to the number of amino groups in the compound of general formula (II) on a mole basis. More preferably, it is 1.0 to 20.0, and more preferably 1.0 to 10.0, on a mole basis. This is because as the amount of the compound of general formula (I) is reduced, the amount of the unreacted portion of the compound of general formula (I) to be removed in the purification step decreases.

Organic Solvent Used in Reaction Step

The organic solvent used in the reaction step is not particularly limited as long as the compound of general formula (I) can be combined with the compound of general formula (II).

Examples of the organic solvent include hydrocarbons such as hexane, cyclohexane and heptane; ketones, such as acetone and methyl ethyl ketone; ethers, such as dimethyl ether, diethyl ether, and tetrahydrofuran; halogenated hydrocarbons, such as dichloromethane, chloroform, carbon tetrachloride, dichloroethane, and trichloroethane; aromatic hydrocarbons, such as benzene and toluene; aprotic polar solvents, such as N,N-dimethylformamide (DMF) and dimethyl sulfoxide (DMSO); and pyridine derivatives. A mixture of these organic solvents may be used.

Aprotic polar solvents, such as DMF and dimethyl sulfoxide, and halogenated hydrocarbons such as dichloromethane and chloroform are advantageous. The compound of general formula (I) is highly soluble in these organic solvents and can come into reaction in a sufficiently dispersed state. The amount of the solvent used in the reaction step may be appropriately set according to the reaction conditions.

The reaction temperature in the reaction step is generally, but is not limited to, 0° C. or more and less than or equal to the boiling point of the solvent. Desirably, the reaction temperature is set to an optimum level for the condensing agent.

The reaction time in the reaction step may be, for example, in the range of 1 to 48 hours.

Purification Step

The purification step in the present embodiment is not particularly limited as long as it is possible to purify the conjugate of a cyanine dye of general formula (I) containing naphthyl groups and a carboxyl or carboxylate group and a compound of general formula (II) containing a polyethylene glycol.

The conjugate produced in the reaction step may be isolated and purified using an organic solvent by normal phase chromatography, gel filtration chromatography, ultrafiltration, or dialysis.

Organic Solvent Used in Purification Step

Examples of the organic solvent used in the purification step include hydrocarbons such as hexane, cyclohexane and heptane; ketones, such as acetone and methyl ethyl ketone; ethers, such as dimethyl ether, diethyl ether, and tetrahydrofuran; halogenated hydrocarbons, such as dichloromethane, chloroform, carbon tetrachloride, dichloroethane, and trichloroethane; aromatic hydrocarbons, such as benzene and toluene; aprotic polar solvents, such as N,N-dimethylformamide and dimethyl sulfoxide; pyridine derivatives; and alcohols, such as methanol and ethanol. A mixture of these organic solvents may be used.

Halogenated hydrocarbons such as dichloromethane and chloroform and alcohols such as methanol and ethanol are advantageous. The cyanine dye of general formula (I) containing naphthyl groups and a carboxyl or carboxylate group and the conjugate are highly soluble in these solvents. Consequently, the purification can be performed in a state where the cyanine dye of general formula (I) and the conjugate are sufficiently dispersed.

It is advantageous that the organic solvent used in the purification step is the same as the organic solvent used in the reaction step.

Drying Step

The drying step may be performed using, but not limited to, an evaporator or a vacuum dryer as used in conventional drying.

Cyanine Dye

The compound or cyanine dye expressed by general formula (I) containing naphthyl groups and a carboxyl or carboxylate group, used in the present embodiment, will now be described.

The cyanine dye has a main skeleton including a methine chain and N-containing 5-membered rings bonded to both ends of the methine chain.

The cyanine dye desirably absorbs light having wavelengths in the range of 600 nm to 1,300 nm and thus emits light. Preferably, the cyanine dye has a molar absorption coefficient of $10^6$ $M^{-1}$ $cm^{-1}$ or more.

Desirably, the cyanine dye of general formula (I) is a compound expressed by the following formula (A):

In formula (A), r and s each represent an integer in the range of 1 to 20. $R_w$ represents an atom selected from the group consisting of hydrogen, sodium and potassium.

More advantageously, the compound of formula (A) is a compound expressed by the following formula (a) (hereinafter referred to as compound (a)):

(a)

Polyethylene Glycol

The compound expressed by general formula (II) containing a polyethylene glycol, used in the present embodiment, will now be described. Preferably, the molecular weight of the compound of general formula (II) is 100 or more from the viewpoint of high dispersibility, and 100,000 or less from the viewpoint of preventing the viscosity of the solution from increasing excessively.

The compound of general formula (II) may be linear or branched in molecular structure. If the compound of (II) is branched, the compound exhibits high dispersibility.

The compound of (II) may contain a plurality of amino groups capable of reacting with the cyanine dye. By binding a plurality of cyanine dye molecules to the compound of (II), the number of bonded cyanine dye molecules per unit polyethylene glycol can be increased.

An example of the compound of general formula (II) containing a polyethylene glycol, used in the present embodiment, may be expressed by the following formula (b-1):

(b-1)

In formula (b-1), t represents an integer in the range of 1 to 2,500. Preferably, the molecular weight of the compound of (b-1) is in the range of 1,000 to 40,000.

Other examples of the compound of (b-1) include SUN-BRIGHT (registered trademark) PA Series (produced by NOF): SUNBRIGHT MEPA-20H, SUNBRIGHT MEPA-50H, SUNBRIGHT MEPA-12T, SUNBRIGHT MEPA-20T, SUNBRIGHT MEPA-30T, and SUNBRIGHT MEPA-40T; SUNBRIGHT (registered trademark) EA Series (produced by NOF): SUNBRIGHT ME-050EA, SUNBRIGHT ME-100EA, SUNBRIGHT ME-200EA (expressed by formula (b-2)), SUNBRIGHT ME-300EA, and SUNBRIGHT ME-400EA; Methoxyl PEG amines (produced by NANOCS): PG1-AM-350, PG1-AM-550, PG1-AM-750, PG1-AM-1k, PG1-AM-2k, and PG1-AM-5k; and SUNBRIGHT GL2-200PA, SUNBRIGHT GL2-400PA, SUNBRIGHT GL2-600PA, SUNBRIGHT GL3-400PA 100U, SUNBRIGHT GL4-600PA, SUNBRIGHT GL4-800PA, SUNBRIGHT PTE-400EA, SUNBRIGHT PTE-400PA (expressed by formula (b-3)), SUNBRIGHT HGEO-150PA, SUNBRIGHT HGEO-400PA, SUNBRIGHT PTE2-200MA2, SUNBRIGHT PTE-400MA2, and SUNBRIGHT PTE-200PA (each produced by NOF).

$$CH_3O-(CH_2CH_2O)_n-CH_2CH_2NH_2 \quad (b\text{-}2)$$

In formula (b-2), the polymerization degree n of the repeating unit is an integer in the range of 1 to 2,500. Preferably, the molecular weight of the compound of (b-2) is in the range of 1,000 to 20,000.

(b-3)

In formula (b-3), X's each represent a group containing an amino group, and the polymerization degree n's of the four repeating units are each an integer in the range of 1 to 2,500. Preferably, the molecular weight of the compound of (b-3) is in the range of 1,000 to 40,000.

Dispersion Medium

The dispersion medium used in the present embodiment may be, for example, physiological saline, distilled water for injection, phosphate buffered saline, or glucose aqueous solution.

Conjugate

The conjugate produced by binding the compound expressed by general formula (I) with the compound expressed by general formula (II) is expressed by the following general formula (III):

(III)

In general formula (III), $R_{201}$ to $R_{212}$ each represent a species selected form the group consisting of hydrogen and linear and branched alkyl groups having a carbon number in the range of 1 to 18. $L_{21}$ to $L_{27}$ each represent CH or $CR_{25}$. $R_{25}$ represents a linear or branched alkyl group having a carbon number in the range of 1 to 18. $L_{21}$ to $L_{27}$ may form one of 4-membered to 6-membered rings. $R_{21}$ to $R_{24}$ each represent a species selected form the group consisting of hydrogen and linear and branched alkyl groups having a carbon number in the range of 1 to 18. $A_{21}$ and $B_{21}$ each represent a linear or branched alkylene group having a carbon number in the range of 1 to 18. $E_{21}$ represents a species selected from the group consisting of hydrogen, linear and branched alkoxy groups having a carbon number in the range of 1 to 18, and linear and branched alkyl groups having a carbon number in the range of 1 to 18. $D_{21}$ represents a linear or branched alkylene group having a carbon number in the range of 1 to 18. Also, q represents an integer in the range of 1 to 20, and p represents an integer in the range of 1 to 2,500.

Contrast Agent for Photoacoustic Imaging

The contrast agent produced by the method of the present embodiment may be used for photoacoustic imaging (PAI). PAI is a concept including photoacoustic tomography (sectional radiography).

EXAMPLES

Although the present invention will be further described with reference to Examples, various modifications to material, composition, reaction conditions and the like may be made effectively without being limited to the following Examples.

Analysis

The structures of the compounds produced in the following Examples were analyzed by $^1$H-NMR using an FT-NMR analyzer (Bruker DPX 600, manufacture by Bruker, resonance frequency: 600 MHz).

The IR spectrometry in each Example was performed with a Fourier transformation infrared absorption spectrometer (FT-IR, NICOLET 8700 manufactured by Thermo Scientific).

The mass spectrometry (MS) for each Example was performed by matrix assisted laser desorption/ionization-mass spectrometry (MALDI-MS) using Autoflex (manufactured by Bruker Daltonics).

Example 1

In 4.0 mL of chloroform were dissolved 50.1 mg of a PEG expressed by formula (b-1) containing an amino group (produced by NANOCS, molecular weight: 1,000) and 59.2 mg of Compound (a) that is a cyanine dye. To the resulting solution was added 14.8 mg of 4-dimethylaminopyridine (DMAP, produced by Tokyo Chemical Industry). To the resulting solution containing DMAP was added 22.8 mg of water-soluble carbodiimide, 1-ethyl-3-(3-dimethylaminopropyl)carbodiimide hydrochloride (abbreviated as WSC, produced by Sigma-Aldrich).

After the resulting solution was stirred at room temperature for 24 hours, the solvent was removed by evaporation.

Then, chloroform was added to the sample from which the solvent had been removed to dissolve the sample again, and the solution of the sample was subjected to separation and purification by normal phase chromatography using particles for silica gel column chromatography (manufactured by Fuji Silysia Chemical) and a mixed solvent of chloroform and methanol.

The solution collected through the separation and purification was subjected to evaporation to remove the solvent, and the product was dried in a vacuum dryer.

The dried product was identified by $^1$H-NMR and MALDI-MS.

Figure 1:
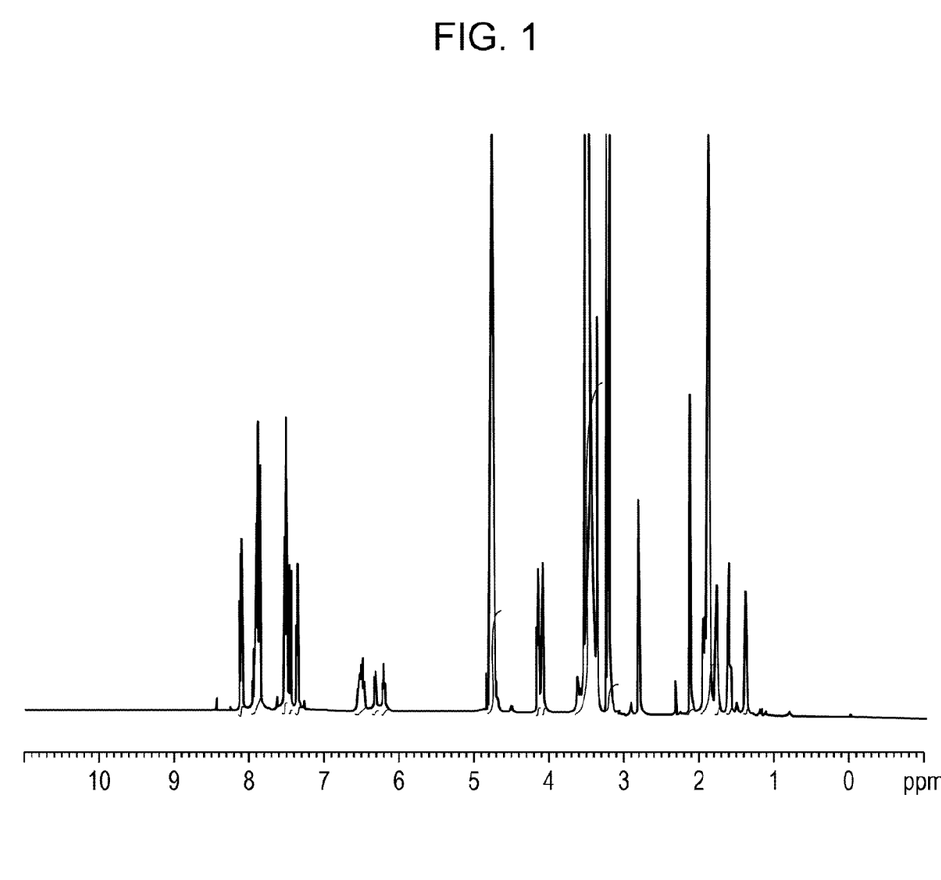
FIG. 1 is a $^1$H-NMR spectrum of the sample produced through purification in Example 1.

The result of $^1$H-NMR analysis is shown in FIG. 1. The $^1$H-NMR result suggests that the final product did not contain unreacted compound (a), and that an intended compound, that is, a conjugate of Compound (a) and the PEG containing an amino group, was produced.

Figure 2:
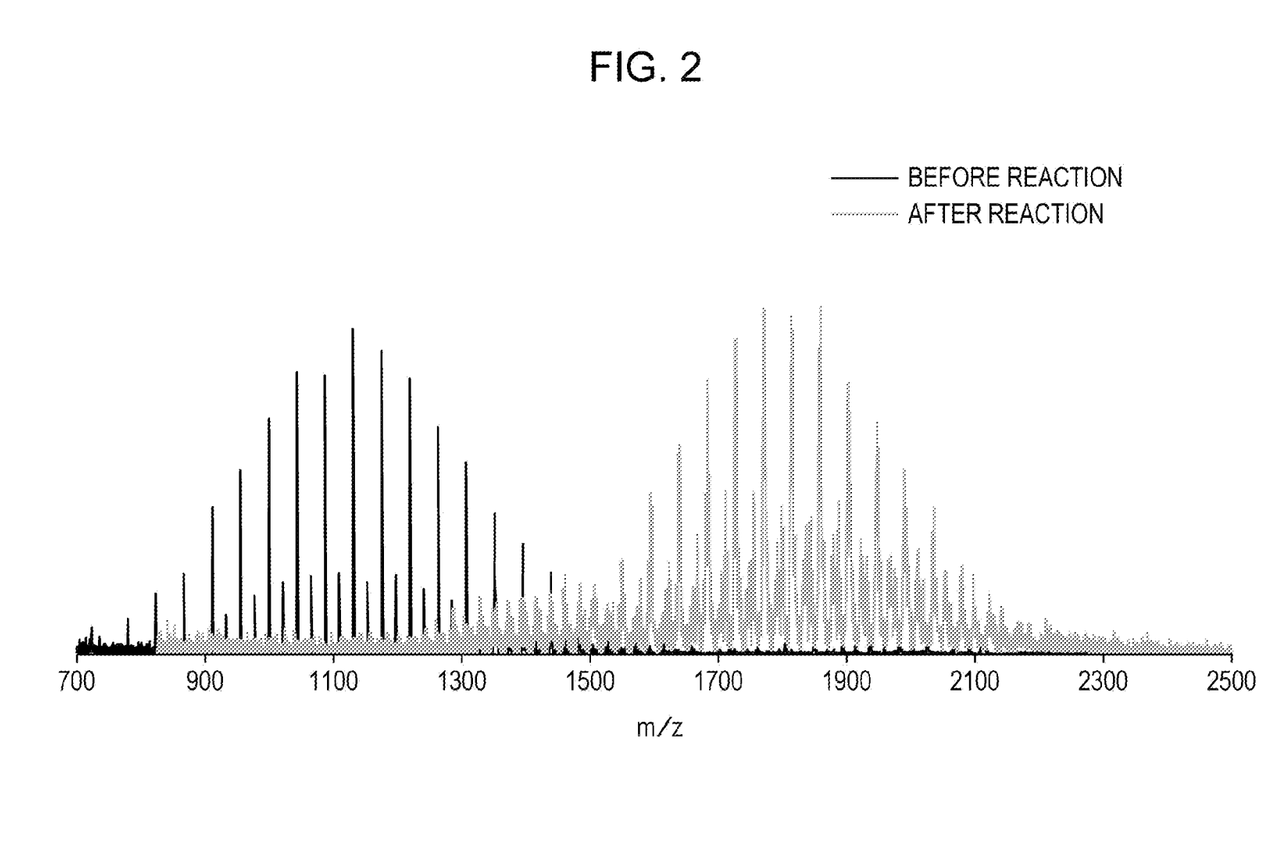
FIG. 2 is MALDI-MS spectra of the sample produced through purification in Example 1.

The results of MALDI-MS analysis are shown in FIG. 2. The MALDI-MS results show a peak shift in molecular weight resulting from a covalent bond of the PEG containing an amino group with Compound (a), and thus it was confirmed that an intended compound was produced.

Example 2

In 2.1 mL of chloroform were dissolved 70 mg of a PEG expressed by formula (b-2) containing an amino group (SUNBRIGHT ME-200EA produced by NOF, molecular weight: 20,000), 5.4 mg of Compound (a) that is a cyanine dye, and 2.8 mg of WSC.

After being stirred at room temperature for 16 hours, the resulting solution was subjected to separation and purification by gel filtration chromatography using a carrier for gel filtration chromatography (LH-20, manufactured by GE Healthcare Japan) and chloroform.

The solution collected through the separation and purification was subjected to evaporation to remove the solvent, and the product was dried in a vacuum dryer.

The dried product was identified by $^1$H-NMR analysis.

Figure 3:
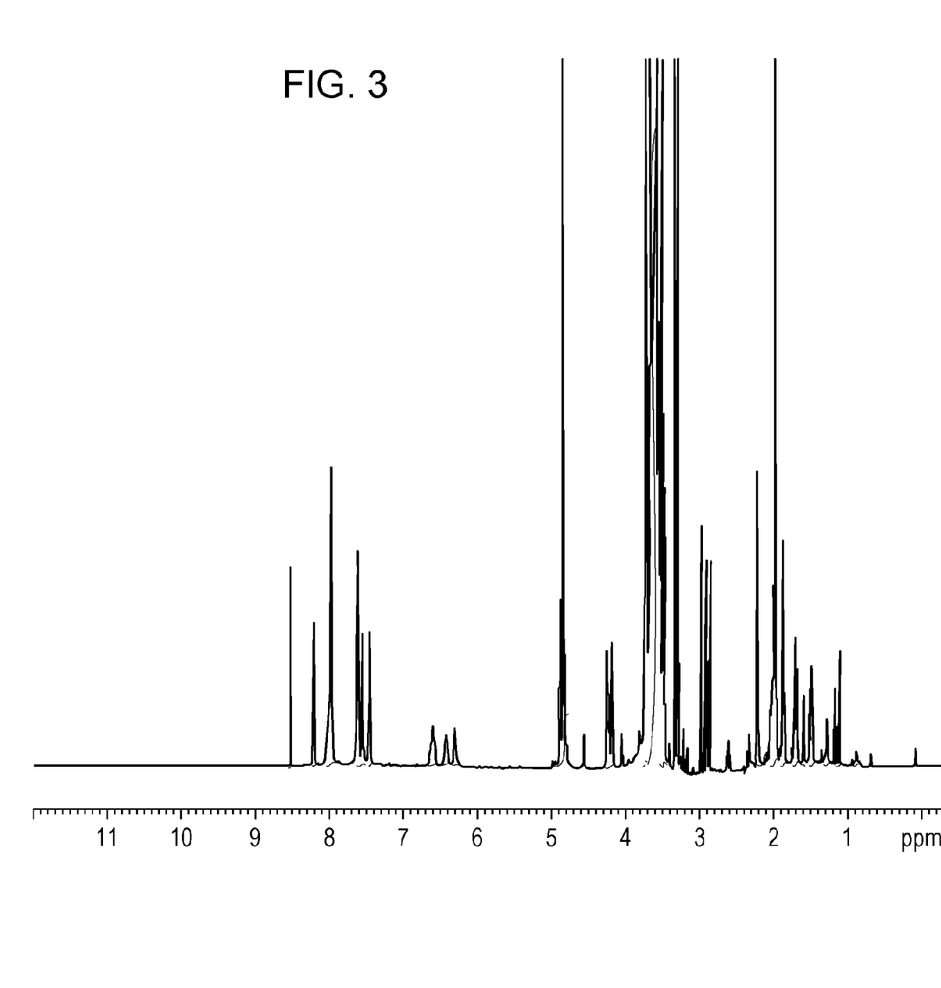
FIG. 3 is a $^1$H-NMR spectrum of the sample produced through purification in Example 2.

The result of $^1$H-NMR analysis is shown in FIG. 3. The $^1$H-NMR result suggests that an intended compound, that is, a conjugate of Compound (a) and the PFG containing an amino group, was produced without containing unreacted Compound (a).

Example 3

In 8.0 mL of DMF were dissolved 50 mg of a PEG expressed by formula (b-3) containing a plurality of amino groups (SUNBRIGHT PTE-400PA produced by NOF, molecular weight: 40,000) and 7.31 mg of Compound (a).

To the resulting solution, a solution of 475 mg of WSC in 120 µL of DMF was added, followed by stirring at room temperature for 24 hours.

Then, 4 mL of thus prepared reaction solution was subjected to separation and purification by dialysis using a dialysis membrane (manufactured by Spectrum Laboratories, molecular weight cut-off: 10,000) and methanol as a solvent.

The solution collected through the separation and purification was subjected to evaporation to remove the solvent, and the product was dried in a vacuum dryer.

The dried product was identified by IR spectrometry.

The result of IR spectrometry showed that the peak at 1716 cm$^{-1}$ derived from the carboxyl group of Compound (a) disappeared, and the presence of the peak at 1665 cm$^{-1}$ derived from the amino group was confirmed. This implies that a conjugate of Compound (a) and the PEG containing amino groups was produced.

Example 4

The results of analysis using various PEGs containing one or more amino groups and cyanine dyes are shown in Table 1. The analysis was performed in the same manner as in Example 3, except that the PEG containing an amino group and the cyanine dye were replaced and that chloroform was used as the solvent.

TABLE 1

| Example | PEG containing amino group | Cyanine dye |
|---|---|---|
| 4-1 | PG1-AM-2k | Compound (a) |
| 4-2 | SUNBRIGHT ME-050EA | Compound (a) |
| 4-3 | SUNBRIGHT ME-100EA | Compound (a) |
| 4-4 | SUNBRIGHT ME-200EA | Compound (a) |
| 4-5 | SUNBRIGHT ME-400EA | Compound (a) |
| 4-6 | SUNBRIGHT PTE-200PA | Compound (a) |
| 4-7 | SUNBRIGHT ME-200EA | Compound (b) |

The results of $^1$H-NMR analysis suggest that intended compounds, that is, conjugates of Compound (a) or (b) and PEGs containing an amino group, were produced without containing unreacted Compound (a) or Compound (b).

Example 5

The results of analysis using various condensing agents are shown in Table 2. The analysis was performed in the same manner as in Example 3, except that the condensing agent and the reaction condition were replaced and that chloroform was used as the solvent.

TABLE 2

| Example | Condensing agent | Reaction temperature | Reaction time | Dye/PEG mole ratio | Condensing agent/PEG mole ratio |
|---|---|---|---|---|---|
| 5-1 | 1-Ethyl-3-(3-dimethylaminopropyl) carbodiimide hydrochloride | Room temperature | 24 hours | 2.0 | 2.0 |
| 5-2 | 1-Ethyl-3-(3-dimethylaminopropyl) carbodiimide hydrochloride | Room temperature | 24 hours | 1.5 | 1.5 |
| 5-3 | 1-Ethyl-3-(3-dimethylaminopropyl) carbodiimide hydrochloride | Room temperature | 2 hours | 2.0 | 2.0 |
| 5-4 | 1-Ethyl-3-(3-dimethylaminopropyl) carbodiimide hydrochloride | Room temperature | 4 hours | 2.0 | 2.0 |
| 5-5 | 1-Ethyl-3-(3-dimethylaminopropyl) carbodiimide hydrochloride | Room temperature | 6 hours | 2.0 | 2.0 |
| 5-6 | 1-Ethyl-3-(3-dimethylaminopropyl) carbodiimide hydrochloride | Room temperature | 6 hours | 2.0 | 2.0 |
| 5-7 | 1-Ethyl-3-(3-dimethylaminopropyl) carbodiimide hydrochloride | 40° C. | 6 hours | 2.0 | 2.0 |
| 5-8 | 1-Ethyl-3-(3-dimethylaminopropyl) carbodiimide hydrochloride | 70° C. | 6 hours | 2.0 | 2.0 |
| 5-9 | N,N'-dicyclohexylcarbodiimide | Room temperature | 24 hours | 2.0 | 2.0 |
| 5-10 | N,N'-dicyclohexylcarbodiimide | Room temperature | 24 hours | 1.5 | 1.5 |

The results of $^1$H-NMR analysis suggest that intended compounds, that is, conjugates of Compound (a) and PFGs containing an amino group, were produced without containing unreacted Compound (a).

The results of Examples 1 to 5 suggest that a conjugate of a cyanine dye tending to form aggregates in water and a PEG can be produced through easy purification.

Comparative Example 1

Comparative Example 1 examined whether or not a cyanine dye tending to form aggregates in water can be purified by reversed phase chromatography using an aqueous solution, as disclosed in the above-cited patent document (PCT Japanese Translation Patent Publication No. 2012-520856).

For purification, a thin-layer chromatography (TLC) plate for reversed phase chromatography (TLC Silica gel plate 60 RP-18 $F_{254}$S manufactured by Merck) was used.

A cyanine dye difficult to form aggregates in water, Cy5 bis-Reactive Dye (produced by GE Healthcare Japan), and Compound (a) tending to aggregate in water were used for comparison.

Spots of these two cyanine dyes were applied onto the TLC plate, and it was observed whether the spots moved from the spotted points.

While the spot of Cy5 bis-Reactive Dye moved up the TLC plate, the spot of Compound (a) did not.

The fact that Compound (a) did not move up the TLC plate suggests that when Compound (a) is subjected to reversed phase chromatography using water, the movement of Compound (a) can stop midway through the column due to the aggregation thereof. Consequently, the conjugate of the cyanine dye or Compound (a) and a PEG, which is considered to be more polar than Compound (a), inevitably passes through the region of the aggregate of Compound (a) before being collected. Thus, it is difficult to discharge only the conjugate. Also, it is expected that the conjugate cannot pass through the column of the reversed phase chromatography due to the presence of the aggregate of Compound (a), and thus cannot be collected.

This suggests that cyanine dyes tending to form aggregates in water such as compound (a) are difficult to purify by reversed phase chromatography using water.

Comparative Example 2

Comparative Example 2 examined whether or not a cyanine dye tending to form aggregates in water can be purified by gel filtration chromatography using an aqueous solution disclosed in Japanese Patent Laid-Open No. 9-124599. For purification, PD-10 column (manufactured by GE Healthcare Japan) was used.

A cyanine dye difficult to form aggregates in water, Cy5 bis-Reactive Dye (produced by GE Healthcare Japan), and Compound (a) tending to aggregate in water were used for comparison.

In the experiment, these two cyanine dyes were separately added to the PD-10 column, and their elution positions in the column were observed.

While the Cy5 bis-Reactive Dye was eluted in a fraction corresponding to low-molecular-weight compounds by gel filtration chromatography, Compound (a) was eluted in both fractions corresponding to polymers and low-molecular-weight compounds. Hence, it is assumed that Compound (a) was eluted in the fraction corresponding to low-molecular-weight compounds, and that the aggregate of Compound (a) having a higher apparent molecular weight was eluted in the fraction corresponding to polymers. The gel filtration chromatography used in this comparative example elutes Compound (a) to a fraction corresponding to low-molecular-weight compounds, and the conjugate of the cyanine dye and PEG to a fraction corresponding to polymers, thereby separating and purifying the conjugate. However, if Compound (a) is eluted to a fraction corresponding to polymers, separation cannot be satisfactorily made.

The results of this comparative example suggest that cyanine dyes tending to form aggregates in water such as Compound (a) are difficult to purify by gel filtration chromatography using water.

In the method for producing a contrast agent according to an embodiment of the present invention, a cyanine dye tending to form aggregates in water is allowed to react with a PEG containing an amino group in an organic solvent, followed by purifying their conjugate using an organic solvent. This method facilitates the purification of the conjugate in comparison with purification techniques using water.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-231576, filed Nov. 7, 2013, which is hereby incorporated by reference herein in its entirety.

What is claimed is:

1. A method for producing a contrast agent containing a conjugate of a compound expressed by general formula (I) and a compound expressed by general formula (II), the method comprising:
   a reaction step of allowing the compound expressed by general formula (I) to react with the compound expressed by general formula (II) to form the conjugate, and
   a purification step of purifying the conjugate using an organic solvent, wherein general formula (I) is:

wherein $R_{101}$ to $R_{112}$ each represent a species selected from the group consisting of hydrogen and linear and branched alkyl groups having a carbon number in the range of 1 to 18, $L_{11}$ to $L_{17}$ each represent a group selected from the group consisting of CH and $CR_{15}$, $R_{15}$ represents an alkyl group selected from the group consisting of linear and branched alkyl groups having a carbon number in the range of 1 to 18, $R_{11}$ to $R_{14}$ each represent a species selected from the group consisting of hydrogen and linear and branched alkyl groups having a carbon number in the range of 1 to 18, $A_{11}$ and $B_{11}$ each represent an alkylene group selected from the group consisting of linear and branched alkylene groups having a carbon number in the range of 1 to 18, and $R_a$ represents an atom selected from the group consisting of hydrogen, sodium and potassium, and wherein general formula (II) is:

wherein $D_{11}$ represents an alkylene group selected from the group consisting of linear and branched alkylene groups having a carbon number in the range of 1 to 18, $E_{11}$ represents a species selected from the group consisting of hydrogen, linear and branched alkoxy groups having a carbon number in the range of 1 to 18, and linear and branched alkyl groups having a carbon number in the range of 1 to 18, m represents an integer in the range of 1 to 20, and n represents an integer in the range of 1 to 2,500.

2. The method according to claim 1, further comprising a drying step of drying a solution containing the conjugate purified in the purification step.

3. The method according to claim 1, wherein the purification step is performed by a technique selected from the group consisting of normal phase chromatography, gel filtration chromatography, ultrafiltration, and dialysis.

4. The method according to claim 1, wherein the compound expressed by general formula (I) is expressed by the following formula (A):

wherein r and s each represent an integer in the range of 1 to 18, and $R_w$ represents an atom selected from the group consisting of hydrogen, sodium and potassium.

5. The method according to claim 4, wherein the compound expressed by formula (A) is expressed by the following formula (a):

(a)

6. The method according to claim 1, wherein the compound expressed by general formula (II) is expressed by the following formula (b-1):

(b-1)

wherein t represents an integer in the range of 1 to 2,500.

7. The method according to claim 1, wherein an organic solvent used in the reaction step is at least one selected from the group consisting of chloroform and dimethylformamide.

8. The method according to claim 1, wherein the organic solvent used in the purification step is at least one selected from the group consisting of chloroform and methanol.

9. The method according to claim 1, wherein the contrast agent is used for photoacoustic imaging.

10. A method for producing a contrast agent containing a conjugate, comprising:

a reaction step of allowing a cyanine dye containing a naphthyl group and at least one of carboxyl and carboxylate groups to react with a polyethylene glycol containing an amino group in an organic solvent to form the conjugate, and a purification step of purifying the conjugate using an organic solvent.

* * * * *